US00PP22659P3

(12) United States Plant Patent
Blom

(10) Patent No.: US PP22,659 P3
(45) Date of Patent: Apr. 17, 2012

(54) ***CHRYSANTHEMUM* PLANT NAMED 'ZANMUAVAL'**

(50) Latin Name: *Chrysanthemum×morifolium Ramat.*
Varietal Denomination: Zanmuaval

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 0 days.

(21) Appl. No.: 12/805,257

(22) Filed: Jul. 21, 2010

(65) Prior Publication Data

US 2012/0023630 P1 Jan. 26, 2012

(51) Int. Cl.
*A01H 5/00* (2006.01)

(52) U.S. Cl. ..... Plt./287

(58) Field of Classification Search ..... Plt./287, Plt./292

See application file for complete search history.

*Primary Examiner* — June Hwu
(74) *Attorney, Agent, or Firm* — Steptoe & Johnson LLP

(57) ABSTRACT

A *chrysanthemum* plant named 'Zanmuaval' characterized by its medium sized blooms with purple ray florets and prolific branching; natural season flower date October 15-22; blooming for a period of 5 weeks.

3 Drawing Sheets

Botanical designation: *Chrysanthemum×morifolium* Ramat.

Cultivar denomination: 'Zanmuaval'.

RELATED CULTIVARS

This new plant cultivar 'ZANMUAVAL' is of the botanical classification *Chrysanthemum×morifolium* Ramat.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmuaval'. 'Zanmuaval' is a product of a breeding and selection program for outdoor pot mums (garden mums) which had the objective of creating new cultivars with a double type inflorescence, a natural season flower date around October 15-22, blooming for a period of 5 weeks. 'Zanmuaval' is a seedling resulting from a crossing program between the female parent id 3384 (non-patented) and male parent id 19455 (non-patented). Plants of the new cultivar 'Zanmuaval' differ from plants of the female parent in the following characteristics. (1) Inflorescence size. And (2) Inflorescence color. (1) The inflorescences of the female parent are smaller in size than those of the new plant. (2) The inflorescences of the female parent are red, while those of the new plant are purple.

Plants of the new cultivar 'Zanmuaval' differ from plants of the male parent in the following characteristics. (1) Vigor. And (2) Susceptibility for white rust. (1) Plants of the male parent are more vigorous than those of the new plant. (2) Plants of the male parent are more susceptible for white rust than those of the new plant.

The new and distinct cultivar was discovered and selected as a flowering plant by Wilhelmus Bernardus Blom on a cultivated field in Rijsenhout, The Netherlands in 2006. The first act of asexual production of 'Zanmuaval' was accomplished when vegetative cuttings from the initial selection in 2006 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
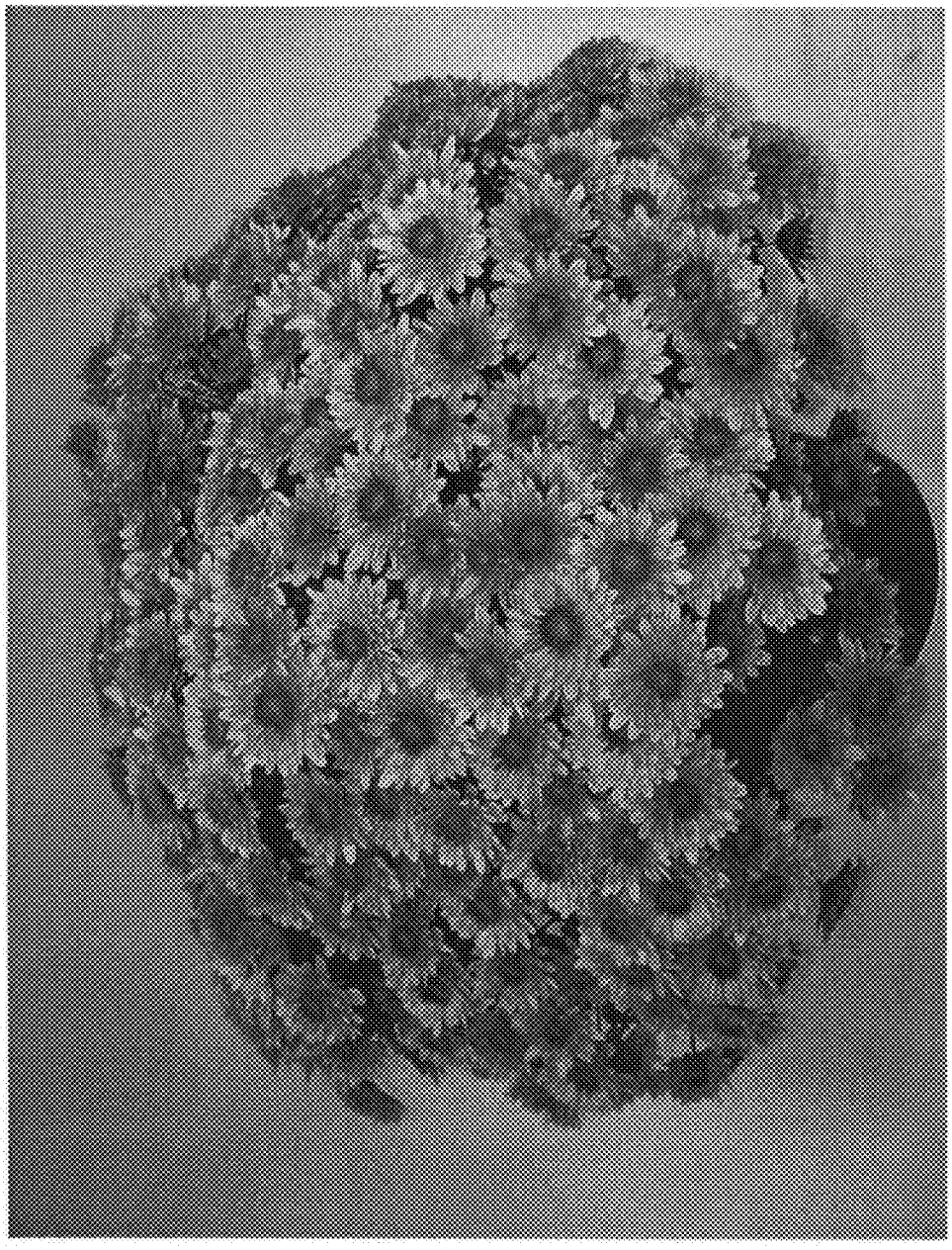
FIG. 1 shows a plant of the cultivar in full bloom.
Figure 2:
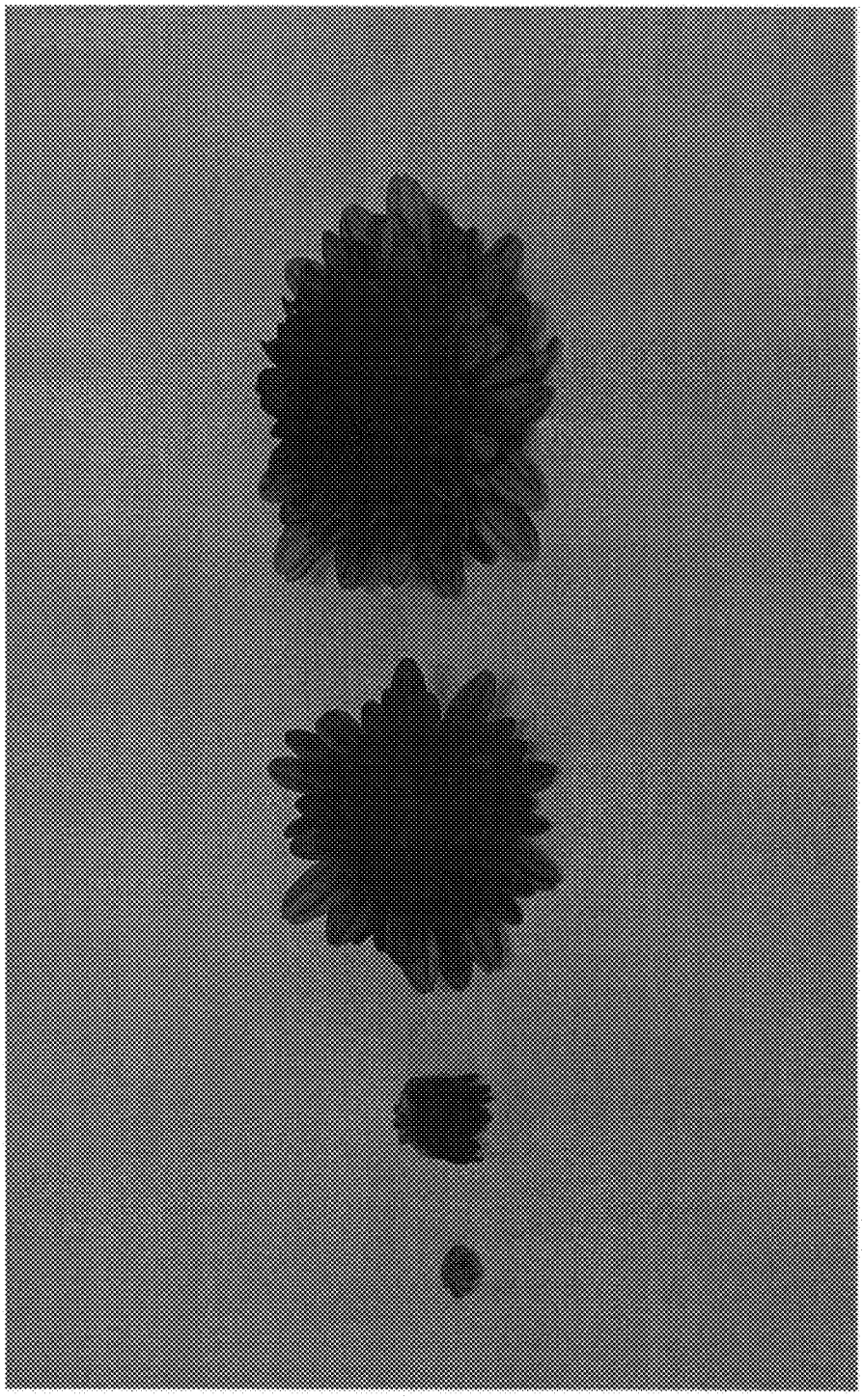
FIG. 2 shows the various stages of bloom of the new cultivar.
Figure 3:
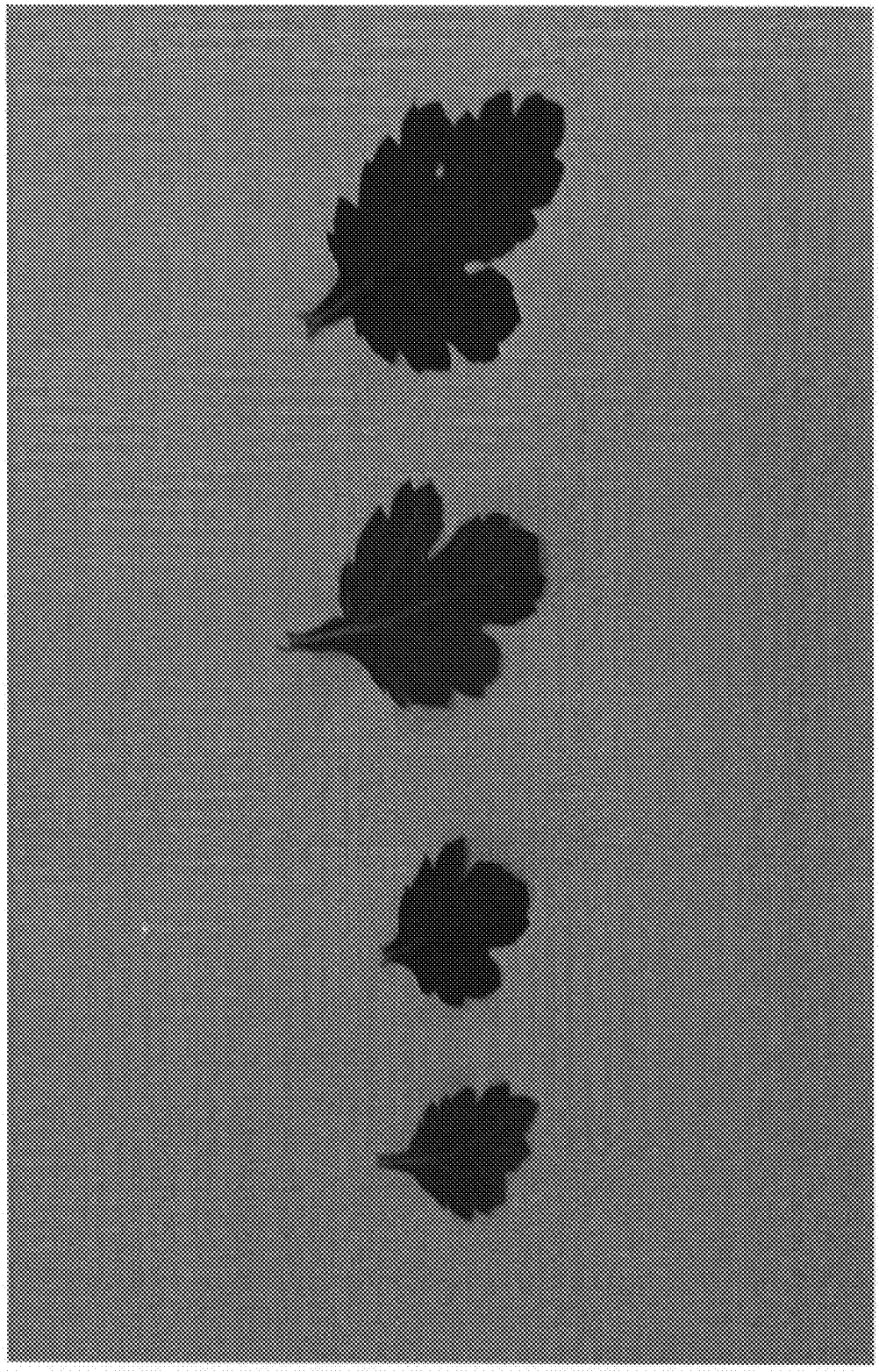
FIG. 3 shows the various stages of foliage of the new cultivar.

The observations and measurements were gathered from plants grown out door in Rijsenhout, The Netherlands under natural day length and temperature and planted in week 23 in 2009. The natural blooming date of this crop was October 15-22 (week 42/43). The average height of the plants was 30 cm. No growth retardants were used. Tests were tested on susceptibility for infection by the fungus white rust *Puccinia horiana.* No tests were done on cold or drought tolerance. This new variety produces medium sized blooms with purple ray florets blooming for a period of 5 weeks.

From the cultivars known to inventor the most similar existing cultivar in comparison to 'Zanmuaval' is 'Venus' (U.S. Plant Pat. No. 14,378). When 'Venus' and 'Zanmuaval' are being compared the following difference is noticed: The difference of 'Venus' and 'Zanmuaval' are (1) natural season blooming date, and (2) difference in tonality of inflorescence color. (1) Plants of 'Venus' flower in an earlier period than those of 'Zanmuaval'. (2) Inflorescences of 'Venus' are evenly purple colored, while those of 'Zanmuval' are more two tone colored, purple with a dark center.

The following is a description of the plant and characteristics that distinguish 'Zanmuaval' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* x *morifolium* Ramat. 'Zanmuaval'

| | |
|---|---|
| Bud | |
| Size | Small; cross-section 0.5 cm, height 0.3 cm |
| Shape | Oblate |
| Texture | Pubescent |
| Outside Color | Greyed-green 191B |
| Phyllaries | |
| Number | 20-22, arranged in 3 rows |
| Shape | Elliptic |
| Apex | Acute |
| Base | Truncate |
| Margin | Entire |
| Color | Upper surface: Greyed-green 191B<br>Lower surface: Green 138A |
| Length and width | 1 cm; 0.1 cm |
| Texture | Pubescent |
| Inflorescence | |
| Type | Double |
| Height | 1.5 cm |
| Diameter | 5 cm |
| Peduncle length | 5-6 cm |
| Peduncle color | Green 138C |
| Peduncle diameter | 0.2 cm |
| Peduncle texture | Pubescent |
| Number per branch | Approx. 6 inflorescences |
| Duration of flowering | 5 weeks |
| Seeds | Produced in small quantities, ovate, Greyed-brown 199A, length 1.5 mm, diameter 0.8 mm |
| Fragrance | Faint chrysanthemum odor |
| Color | |
| Center of inflorescences | Immature stage: Purple N79B<br>Mature stage: Purple N79D |
| Color of upper surface of the ray-florets | Purple N79C |
| Color of the lower surface of the ray-florets | Purple 77C |
| Tonality from Distance | A garden mum with purple flowers with a dark center |
| Color of the ray-florets after aging of the plant | Purple 77D |
| Ray florets | |
| Texture | Upper and lower surface smooth |
| Number | 240-260 |
| Shape | Elliptic |
| Apex | Varying from acute to dentate |
| Base | Attenuate |
| Cross-section | Flat |
| Longitudinal axis of majority | Straight |
| Length of corolla tube | 0.2-0.4 cm |
| Ray-floret margin | Entire |
| Ray-floret length | 1-2.5 cm |
| Ray-floret width | 0.2-0.5 cm |
| Ratio length/width | High |
| Disc florets | Absent |

TABLE 1-continued

Botanical Description of *Chrysanthemum* x *morifolium* Ramat. 'Zanmuaval'

| | |
|---|---|
| Receptacle | |
| Color | Green 138C |
| Shape | Domed raised |
| Height | 0.3 cm |
| Diameter | 0.4 cm |
| Reproductive Organs | |
| Androecium | Absent |
| Pollen | Not produced |
| Gynoecium | Present in ray-florets |
| Style Length | 3 mm |
| Stigma color | Yellow 7A |
| Stigma Width | 1 mm |
| Ovary | Enclosed in calyx |
| Plant | |
| Form | Grown as a spray type pot mum, outdoor raised and mounded |
| Growth habit | Spherical shape |
| Growth rate | Medium |
| Height | 30 cm |
| Width | 50 cm |
| Stem Color | Greyed-brown 199A |
| Stem Strength | Weak |
| Stem Brittleness | Brittle |
| Stem Anthocyanin Coloration | Not observed |
| Internode length | 2-4 cm |
| Length of lateral branch | From top to bottom 20 cm |
| Lateral branch color | Green 137C |
| Lateral branch, attachment | Brittle |
| Lateral branch diameter | 2 mm |
| Branching (average number of lateral branches) | Prolific with 8-9 breaks after pinching |
| Natural season blooming date | October 15-22 (week 42/43) |
| Foliage | |
| Leaf color | Upper side: Green 139A<br>Lower side: Green N138A |
| Color midvein | Upper side: Yellow-green 147D<br>Lower side: Yellow-green 148D |
| Size | Small.; length 3-5 cm, width 2-3.5 cm |
| Quantity (number per lateral branch) | 15-17 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Truncate |
| Apex | Mucronulate |
| Petiole length | 0.3-0.8 cm |
| Petiole diameter | 0.2-0.4 cm |
| Petiole color | Yellow-green 147D |

TABLE 2

Differences with the comparison variety

| | 'Zanmuaval' | 'Venus' |
|---|---|---|
| Natural season blooming date | Week 42/43 | Week 35 |
| Color center inflorescence | Purple N79B | Red-purple 60A |
| Color upper surface ray florets | Purple N79C | Red-purple 60A |

I claim:

1. A new and distinct *chrysanthemum* plant named 'Zanmuaval' as described and illustrated.

* * * * *